(12) United States Patent
Densham

(10) Patent No.: US 6,908,736 B1
(45) Date of Patent: Jun. 21, 2005

(54) DNA SEQUENCING METHOD

(75) Inventor: Daniel Henry Densham, Devon (GB)

(73) Assignee: Medical Biosystems, Ltd. (GB)

(*) Notice: Subject to any disclaimer, the term of this patent is extended or adjusted under 35 U.S.C. 154(b) by 0 days.

(21) Appl. No.: 10/089,877

(22) PCT Filed: Oct. 6, 2000

(86) PCT No.: PCT/GB00/03860

§ 371 (c)(1),
(2), (4) Date: Aug. 8, 2002

(87) PCT Pub. No.: WO01/25480

PCT Pub. Date: Apr. 12, 2001

(30) Foreign Application Priority Data

Oct. 6, 1999 (GB) .............................. 9923664

(51) Int. Cl.⁷ .......................... C12Q 1/68; C12N 11/16; C12N 5/00; C07H 21/00; C07H 21/04
(52) U.S. Cl. .......................... 435/6; 435/174; 435/402; 536/23.1; 536/25.32; 536/23.2
(58) Field of Search .......................... 435/6, 174, 402, 435/91.1, 91.2, 195; 536/23.1, 25.32, 23.2

(56) References Cited

U.S. PATENT DOCUMENTS

| | | | |
|---|---|---|---|
| 5,360,714 A | 11/1994 | Seeger | |
| 5,620,854 A | 4/1997 | Holzrichter et al. | |
| 5,747,247 A | 5/1998 | Kowalczykowski et al. | |
| 5,753,439 A | 5/1998 | Smith et al. | |
| 5,801,042 A | 9/1998 | Chang et al. | |
| 6,159,687 A | 12/2000 | Vind | |
| 6,210,896 B1 * | 4/2001 | Chan .............................. | 435/6 |
| 6,221,642 B1 | 4/2001 | O'Donnell | |
| 6,263,286 B1 | 7/2001 | Gilmanshin et al. | |
| 6,331,392 B1 * | 12/2001 | Laing et al. ..................... | 435/6 |
| 6,355,420 B1 * | 3/2002 | Chan .............................. | 435/6 |
| 2003/0044781 A1 * | 3/2003 | Korlach et al. ................. | 435/6 |

FOREIGN PATENT DOCUMENTS

| | | |
|---|---|---|
| WO | WO 90/05303 | 5/1990 |
| WO | WO 90/13666 | 11/1990 |
| WO | WO 91/06678 | 5/1991 |
| WO | WO 93/21340 | 10/1993 |
| WO | WO 94/21822 | 9/1994 |
| WO | WO 95/06138 * | 3/1995 |
| WO | WO 99/05315 | 2/1999 |
| WO | WO 00/09757 | 2/2000 |
| WO | WO 00/53805 | 9/2000 |
| WO | WO 00/60114 | 10/2000 |

OTHER PUBLICATIONS

Ha et al. Single–Molecule fluorescence spectroscopy of enzyme confromational dynamics and cleavage mechanism. Proc. Natl. Acad. Sci. USA, vol. 96, pp. 893–898, Feb. 1999.*

Ha et al Proc. Natl. Acad. Sci. USA, vol. 96, pp. 893–898, Feb. 1996.*

Schwarz, T., et al., "Detection of nucleic acid hybridization using surface plasmon resonance", *Tibtech* (1991), pp. 333–340, vol. 9; Elsevier Science Publishers Ltd., U.K.

Sutton, M., et al., "*Ercherichia coli* DnaA Protein", *J. Biol. Chem.* (1998), pp. 34255–34262, vol. 273, No. 51, The American Society for Biochemistry and Molecular Biology, Inc., U.S.A.

Furey, S. et al. "Use of Fluorescence Resonance Energy Transfer to Investigate the Conformation of DNA Substrates Bound to the Klenow Fragment" *Biochemistry* (1998), 37:2979–2990; XP–002171248.

Ha, T. et al. "Probing the interaction between two single molecules: Fluorescence resonance energy transfer between a single donor and a single acceptor" *Proc. Natl. Acad. Sci. USA* (1996), 93:6264–6268; XP–002171249.

Ha, T. et al. "Single–molecule fluorescence spectroscopy of enzyme conformational dynamics and cleavage mechanism" *Proc. Natl. Acad. Sci. USA* (1999), 96:893–898; XP–002171247.

Weiss, S. "Fluorescence Spectroscopy of Single Biomolecules" *Science* (1999), 283:1676–1683; XP–002171250.

* cited by examiner

Primary Examiner—Kenneth R. Horlick
Assistant Examiner—Cynthia B. Wilder
(74) Attorney, Agent, or Firm—Saliwanchik, Lloyd & Saliwanchik

(57) ABSTRACT

The present invention pertains to a method for determining the sequence of a polynucleotide, the method relying on the detection of a conformational change in an enzyme that interacts with and processes along the polynucleotide. The detection of a conformational change may be carried out by measuring changes in a fluorophore bound to the enzyme.

15 Claims, 2 Drawing Sheets

US 6,908,736 B1

DNA SEQUENCING METHOD

FIELD OF THE INVENTION

This invention relates to polynucleotide sequence determinations.

BACKGROUND OF THE INVENTION

The ability to determine the sequence of a polynucleotide is of great scientific importance. For example, the Human Genome Project is an ambitious international effort to map and sequence the three billion bases of DNA encoded in the human genome. When complete, the resulting sequence database will be a tool of unparalleled power for biomedical research. The major obstacle to the successful completion of this project concerns the technology used in the sequencing process.

The principle method in general use for large-scale DNA sequencing is the chain termination method. This method was first developed by Sanger and Coulson (Sanger et al., Proc. Natl. Acad. Sci. USA, 1977; 74: 5463–5467), and relies on the use of dideoxy derivatives of the four nucleoside triphosphates which are incorporated into a nascent polynucleotide chain in a polymerase reaction. Upon incorporation, the dideoxy derivatives terminate the polymerase reaction and the products are then separated by gel electrophoresis and analysed to reveal the position at which the particular dideoxy derivative was incorporated into the chain.

Although this method is widely used and produces reliable results, it is recognised that it is slow, labour-intensive and expensive.

An alternative sequencing method is proposed in EP-A-0471732, which uses spectroscopic means to detect the incorporation of a nucleotide into a nascent polynucleotide strand complementary to a target. The method relies on an immobilised complex of template and primer, which is exposed to a flow containing only one of the different nucleotides. Spectroscopic techniques are then used to measure a time-dependent signal arising from the polymerase catalysed growth of the template copy. The spectroscopic techniques described are surface plasmon resonance (SPR) spectroscopy, which measures changes in an analyte within an evanescent wave field, and fluorescence measuring techniques. However, limitations of this method are recognised; the most serious for the SPR technique being that, as the size of the copy strand grows, the absolute size of the signal also grows due to the movement of the strand out of the evanescent wave field, making it harder to detect increments. The fluorescence measuring techniques have the disadvantage of increasing background interference from the fluorophores incorporated on the growing nascent polynucleotide chain. As the chain grows, the background "noise" increases and the time required to detect each nucleotide incorporation needs to be increased. This severely restricts the use of the method for sequencing large polynucleotides.

Single fragment polynucleotide sequencing approaches are outlined in WO-A-9924797 and WO-A-9833939, both of which employ fluorescent detection of single labelled nucleotide molecules. These single nucleotides are cleaved from the template polynucleotide, held in a flow by an optical trap (Jett, et al., J. Biomol. Struc. Dyn, 1989; 7:301–309), by the action of an exonuclease molecule. These cleaved nucleotides then flow downstream within a quartz flow cell, are subjected to laser excitation and then detected by a sensitive detection system. However, limitations of this method are recognised; the most serious for the exonuclease technique being the fact that the labelled nucleotides severely affect the processivity of the exonuclease enzyme. Other limitations of this method include 'sticking' of the nucleotide(s) to the biotin bead used to immobilise the polynucleotide fragment, thus resulting in the nucleotide flow becoming out of phase; inefficiency and length limitation of the initial enzymatic labelling process; and the excitation 'cross-over' between the four different dye molecules resulting in a greatly increased error rate.

There is therefore a need for an improved method, preferably at the single fragment level, for determining the sequence of polynucleotides, which significantly increases the rate and fragment size of the polynucleotide sequenced and which is preferably carried out by an automated process, reducing the complexity and cost associated with existing methods.

SUMMARY OF THE INVENTION

The present invention is based on the realisation that the sequence of a target polynucleotide can be determined by measuring conformational changes in an enzyme that binds to and processes along the target polynucleotide. The extent of the conformational change that takes place is different depending on which individual nucleotide on the target is in contact with the enzyme.

According to one aspect of the present invention, a method for determining the sequence of a polynucleotide comprises the steps of:

(i) reacting a target polynucleotide with an enzyme that is capable of interacting with and precessing along the polynucleotide, under conditions sufficient to induce the enzyme activity; and (ii) detecting conformational changes in the enzyme as the enzyme processes along the polynucleotide.

In a preferred embodiment, the enzyme is a polymerase enzyme which interacts with the target in the process of extending a complementary strand. The enzyme is typically immobilised on a solid support to localise the reaction within a defined area.

According to a second embodiment of the invention, the enzyme comprises a first bound detectable label, the characteristics of which alter as the enzyme undergoes a conformational change. The enzyme may also comprise a second bound detectable label capable of interacting with the first label, wherein the degree of interaction is dependent on a conformational change in the enzyme. Typically, the first label is an energy acceptor and the second label is an energy donor, and detecting the conformational change is carried out by measuring energy transfer between the two labels.

According to a further embodiment of the invention, fluorescence resonance energy transfer (FRET) is used to detect a conformational change in an enzyme that interacts with and processes along a target polymerase, thereby determining the sequence of the polynucleotide. Fluorescence resonance energy transfer may be carried out between FRET donor and acceptor labels, each bound to the enzyme. Alternatively, one of the labels may be bound to the enzyme and the other label bound to the polynucleotide.

According to a further embodiment, there is the use of a detectably-labelled enzyme, capable of interacting with and precessing along a target polynucleotide, to determine the sequence of the polynucleotide, wherein the label alters its detectable characteristics as the enzyme processes along the polynucleotide.

According to a further aspect, a solid support comprises at least one immobilised enzyme capable of interacting with and precessing along a target polynucleotide, the enzyme being labelled with one or more detectable labels.

According to a further aspect, a system for determining the sequence of a polynucleotide comprises a solid support as defined above, and an apparatus for detecting the label.

The present invention offers several advantages over conventional sequencing technology. Once a polymerase enzyme begins its round of polynucleotide elongation, it tends to polymerase several thousand nucleotides before falling off from the strand. Additionally, certain specific polymerase systems are able to anchor or tether themselves to the template polynucleotide via a 'sliding clamp' (e.g. Polymerase III) which encircles the template molecule or via a molecular hook (e.g. T7:thireodoxin complex) which partially encircles the template.

The invention may also enable tens of kilobases (kb) or more to be sequenced in one go, at a rate of hundreds of base pairs per second. This is a result of sequencing on a single fragment of DNA. An advantage of sequencing a single fragment of DNA is that sequencing rates are determined by the enzyme system utilised and not upon indirect, summated reactions, and are therefore correspondingly higher. Just as important as the high rate is the ability to sequence large fragments of DNA. This will significantly reduce the amount of subcloning and the number of overlapping sequences required to assemble megabase segments of sequencing information. An additional advantage of the single fragment approach is the elimination of problems associated with the disposal of hazardous wastes, such as acrylamide, which plague current sequencing efforts.

DESCRIPTION OF THE INVENTION

Figure 1:
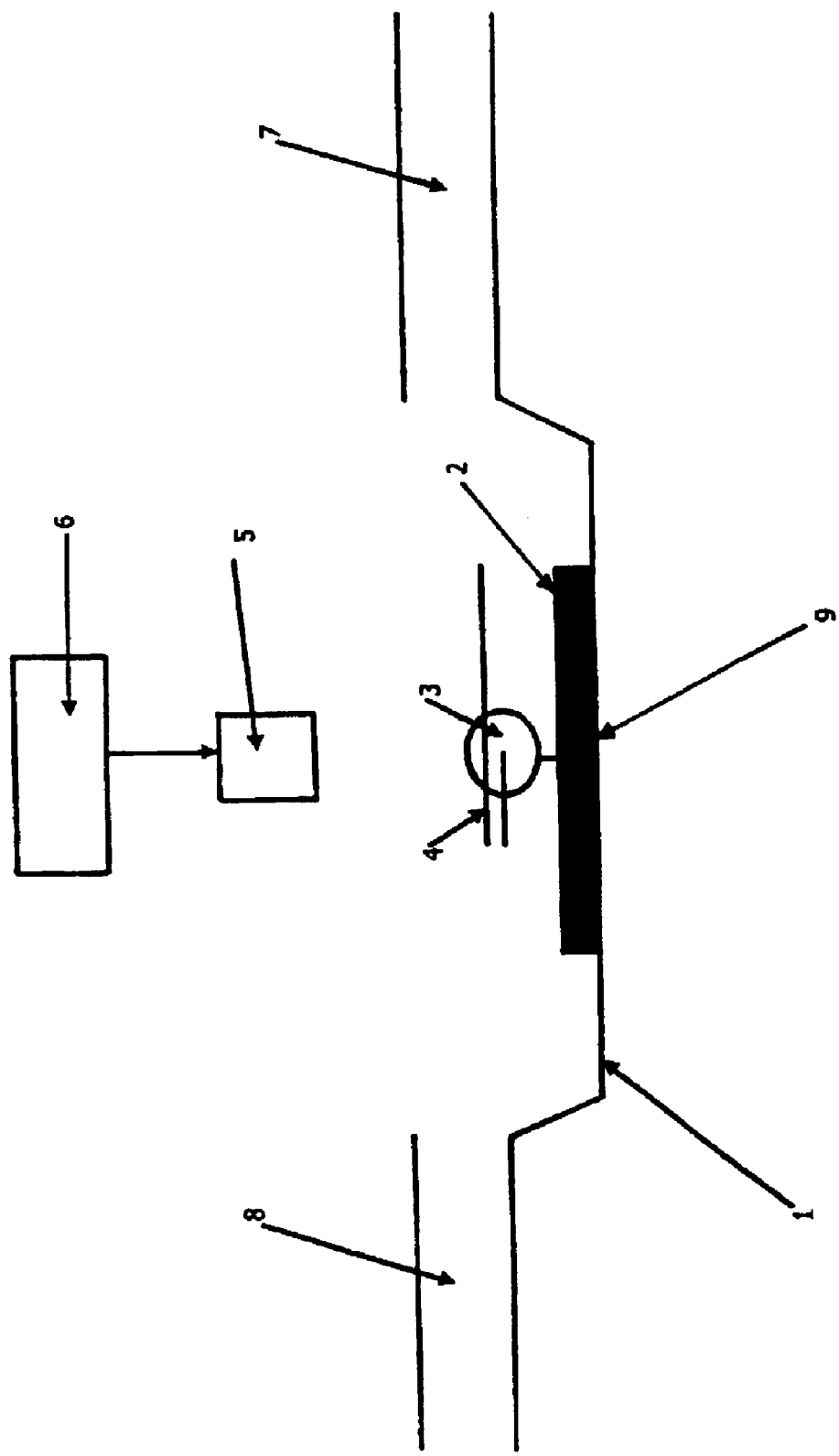
FIG. 1 is a schematic illustration of a confocal microscope setup for use in the invention.

The present method for sequencing a polynucleotide involves the analysis of conformational changes between an enzyme and a target polynucleotide.

The term "polynucleotide" as used herein is to be interpreted broadly, and includes DNA and RNA, including modified DNA and RNA, as well as other hybridising nucleic acid-like molecules, e.g. peptide nucleic acid (PNA).

The enzyme may be a polymerase enzyme, and a conformational change is brought about when the polymerase incorporates a nucleotide into a nascent strand complementary to the target polynucleotide. It has been found that the conformational change will be different for each of the different nucleotides, A, T, G or C and therefore measuring the change will identify which nucleotide is incorporated.

Alternatively, the enzyme may be any that is involved in an interaction with a polynucleotide, e.g. a helicase enzyme, primase and holoenzyme. As the enzyme processes along the polynucleotide, its conformation will change depending on which nucleotide on the target it is brought into contact with.

One way of detecting a conformational change in the enzyme is to measure resonance energy transfer between a suitable energy donor label and a:suitable energy acceptor label. In one example the donor and acceptor are each bound to the enzyme and the conformational change in the enzyme brought about by its interaction with the target polynucleotide alters the relative positioning of the labels. The differences in positioning are reflected in the resulting energy transfer and are characteristic of the particular nucleotide in contact with the enzyme. Alternatively, one label may be positioned on the enzyme and the other on a nucleotide of the target or on a nucleotide incorporated onto a strand complementary to the target.

The use of fluorescence resonance energy transfer (FRET) is a preferred embodiment of the invention. This technique is capable of measuring distances on the 2- to 8 nm scale and relies on the distance-dependent energy transfer between a donor fluorophore and an acceptor fluorophore. The technique not only has superior static co-localization capabilities but can also provide information on dynamic changes in the distance or orientation between the two fluorophores for intramolecular and intermolecular FRET. Since the first measurement of energy transfer between a single donor and a single acceptor (single pair FRET) (Ha, et al., Proc. Natl. Acad. Sci. USA, 1996; 96:893), it has been used to study ligand-receptor co-localisation (Schutz, et al., Biophys. J., 1998; 74:2223), to probe equilibrium protein structural fluctuations and enzyme-substrate interactions during catalysis (Ha, et al., 1999 Supra), and to identify conformational states and sub-populations of individual diffusing molecules in solutions. All of these variables are envisioned as applicable within the context of the invention.

The present invention may also be carried out using measurement techniques that require only a single label. Any system that is capable of measuring changes in the local environment of the enzyme at the single molecule level, is an accepted embodiment of the invention. Various properties of single fluorescent probes attached to a polynucleotide processive enzyme and/or its substrate(s) can be exploited in the context of the invention to provide data on variables within or in close proximity to the enzyme system/molecular environment that are specific to a nucleotide incorporation event. Such variables include, but are not limited to, molecular interactions, enzymatic activity, reaction kinetics, conformational dynamics, molecular freedom of motion, and alterations in activity and in chemical and electrostatic environment.

For example, the absorption and emission transition dipoles of single fluorophores can be determined by using polarized excitation light or by analysing the emission polarisation, or both. The temporal variation in dipole orientation of a rigidly attached or rotationally diffusing tethered label can report on the angular motion of a macromolecule system or one of its subunits (Warshaw, et al., Proc. Natl. Acad. Sci. USA, 1998; 95:8034) and therefore may be applied in the present invention.

The labels that may be used in the present invention will be apparent to those skilled in the art. Preferably, the label is a fluorescence label, such as those disclosed in Xue, et al., Nature, 1995; 373:681. Alternatively, fluorescing enzymes such as green fluorescent protein (Lu, et al., Science, 1998; 282:1877) can be employed.

The preferred embodiment of the invention, however, involves the use of small fluorescence molecules that are covalently and site-specifically attached to the polynucleotide processive enzyme, e.g. tetramethylrhodamine (TMR).

If fluorescent labels are used in the invention, their detection may be affected by photobleaching caused by repeated exposure to excitation wavelengths. One possible way to avoid this problem is to carry out many sequential reactions, but detecting fluorescence signals on only a few at a time. Using this iterative process, the correct sequence of signals can be determined and the polynucleotide sequence determined. For example, by immobilising a plurality of enzymes on a solid support and contacting them with the target polynucleotide, the sequencing reactions should start at approximately the same time. Excitation and detection of fluorescence can be localised to a proportion of the total reactions, for a time until photobleaching becomes evident. At this time, excitation and detection can be transferred to a different proportion of the reactions to continue the sequencing. As all the reactions are relatively in phase, the correct sequence should be obtained with minimal sequence re-assembly.

The labels may be attached to the enzymes by covalent or other linkages. A number of strategies may be used to attach the labels to the enzyme. Strategies include the use of site-directed mutagenesis and unnatural amino acid mutagenesis (Anthony-Cahil' et al., Trends Biochem. Sci., 1989; 14:400) to introduce cysteine and ketone handles for specific and orthogonal dye labelling proteins (Cornish, et al., Proc. Natl. Acad. Sci. USA, 1994; 91:2910).

Another foreseen embodiment used to tag the polynucleotide processive enzyme is the fusion of green fluorescent protein (GFP) to the processive enzyme (e.g. polymerase) via molecular cloning techniques known in the art (Pierce, D. W. et al., Nature, 1997; 388:338). This technique has been demonstrated to be applicable to the measurement of conformational changes (Miyawaki, et al., Nature, 1997; 388:882) and local pH changes (Llopis, et al., Proc. Natl. Acad. Sci. USA, 1998; 95:6803).

Supports suitable for use in immobilising the enzymes, will be apparent to the skilled person. Silicon, glass and ceramics materials may be used. The support will usually be a planar surface. Enzyme immobilisation may be carried out by covalent or other means. For example, covalent linker molecules may be used to attach to a suitably prepared enzyme. Attachment methods are known to the skilled person.

There may be one or more enzymes immobilised to the solid support. In a preferred embodiment, there are a plurality of enzymes attached. This allows monitoring of many separate reactions, and may be useful to overcome photobleaching problems as outlined above.

A variety of techniques may be used to measure a conformational change in the enzyme. Resonance energy transfer may be measured by the techniques of surface plasmon resonance (SPR) or fluorescent surface plasmon resonance. However, other techniques which measure changes in radiation via interaction with a 'label' or energy transducer may be considered, for example spectroscopy by total internal reflectance fluorescence (TIRF), attenuated total reflection (ATR), frustrated total reflection (FTR), Brewster angle reflectometry, scattered total internal reflection (STIR), fluorescence lifetime imaging microscopy and spectroscopy (FLIMS), fluorescence polarisation anisotrophy (FPA), fluorescence spectroscopy, or evanescent wave ellipsometry.

The invention will now be illustrated further by the following Example, with reference to the accompanying drawings.

EXAMPLE

This Example used a confocal fluorescence setup, as shown in FIG. 1.

With reference to FIG. 1, the setup consists of a scan table (1) able to scan at high resolution in X, Y and Z dimensions, a class coverslip (2) which is part of a microfluidic flow cell system with an inlet (8) for introducing the primer-template polynucleotide complex (4) and nucleotides over the immobilised (9) polymerase molecule (3) within a buffer, and an outlet (7) for waste. Incident light from a laser light source (6) for donor excitation is delivered via an oil-immersion objective (5).

Protein Conjugation

In this experiment, Tetramethylrhodamine (TMR, donor) and Cy5 (acceptor) where used as the FRET pair. This was due to their well separated emission wavelengths (>100 nm) and large Föster radius.

T7 DNA Polymerase from New England Biolabs (supplied at 10 000 U/ml) was used. 50 $\mu$l of T7 was buffer-exchanged in a Vivaspin 500 (Vivaspin) against 4×500 $\mu$l of 200 mM Sodium Acetate buffer at pH 4 in order to remove the DTT from the storage buffer that the T7 DNA Polymerase is supplied in. Then, 50 $\mu$l of the buffer-exchanged T7 DNA polymerase was added to 100 $\mu$l of Sodium Acetate buffer at pH 4 and 50 $\mu$l saturated 2-2-DiPyridyl-DiSulphide in aqueous solution. This reaction was then left for 110 minutes and the absorption at 343 nm noted. Finally, the sample was then buffer-exchanged into 200 mM Tris at pH 8 as before (4 times 500 $\mu$l).

Dye attachment was verified by denaturing polyacrylamide gel electrophoresis. Cy5 succinimidyl ester (Molecular Probes) was conjugated to the TMR-T7 DNA Polymerase under the same labelling conditions and purified and characterized as described above.

Polymerase Immobilization

Glass coverslips were derivatized with N-[(3-trimethoxysilyl)propyl] ethylenediamine triacetic acid. The coverslip was then glued into a flow-cell arrangement that allowed buffer to be flowed continuously over the derivatized glass surface. The labelled polymerase was then added to the buffer and allowed to flow over the coverslip so that protein was immobilised on the glass surface.

Proteins were then immobilised on the glass-water interface with low density so that only one molecule was under the laser excitation volume at any one time. Laser light (514 nm Ar ion laser, 15 $\mu$W, circularly polarized) was focused onto a 0.4 $\mu$m spot using an oil immersion objective in an epi-illumination setup of a scanning-stage confocal microscope. The fluorescence emission was collected by the same objective and divided into two by a dichroic beam splitter (long pass at 630 nm) and detected by two Avalanche Photo Diode (APD) counting units, simultaneously.

A 585 nm band pass filter was placed in front of the donor detector; a 650 nm long pass filter was placed in front of the acceptor detector. Since the spectral ranges during fluorescence detection are sufficiently removed from the cutoff wavelength of the dichroic beam splitter, the polarization dependence of the detection efficiency of both donor and acceptor signal is negligible. It has been shown that the polarization mixing due to the high near field aperture (NA) objective can be overlooked (Ha et al, Supra).

In order to acquire donor and acceptor emission times, a search condition on the acceptor signal was employed as outlined in (Ha, et al., Appl. Phys. Lett., 1997; 70:782). This procedure aids in the screening of doubly labelled proteins: with no direct excitation of the acceptor, only proteins experiencing FRET could show acceptor signal. Once a protein was screened, located and positioned under the laser spot, donor and acceptor time traces (5 ms integration time) were acquired. The acquisition time lasted until all the fluorescent labels on the target protein where photobleached.

Reaction Initiation

Two oligonucleotides were synthesised using standard phosphoramidite chemistry. The oligonucleotide defined as SEQ ID NO: 1 was used as the target polynucleotide, and the oligonucleotide defined as SEQ ID NO: 2 was used as the primer. The two oligonucleotides were reacted under hybridizing conditions to form the target-primer complex.

CAAGGAGAGGACGCTGTCTGTCGAAGGTAAGGAACGGACGAGAGAAGGGAGAG    SEQ ID NO: 1

CTCTCCCTTCTCTCGTC    SEQ ID NO: 2

The reaction was then initiated by injecting the primed DNA into the flow cell with all four nucleotides (dGTP, dCTP, dATP and dTTP) present at a concentration of 0.4 mM. The flow cell was maintained at 25 degrees Celsius by a modified peltier device.

An oxygen-scavenging system was also employed [50 µg/ml glucose oxidase, 10 µg/ml catalase, 18% (wt/wt) glucose, 1% (wt/vol) β-mercaptoethanol] to prolong fluorescent lifetimes (Funatsu, et al., Nature, 1995; 374:555–559).

FRET Data Analysis

Initial studies have determined the origins of blinking, photobleaching and triplet state spikes (Ha, et al., Chem. Phy., 1999; 247:107–118), all of which can interfere with the underlying changes in FRET efficiency, due to distance changes between fluorophores as a result of conformational changes. After subtracting the background signal from donor and acceptor time traces as disclosed in Ha, et al., 1999 (Supra), a median filter, with five points average, was applied to remove triplet spikes. Next, data points that showed simultaneous dark counts on both detectors due to donor blinking events were disregarded from the time traces.

The amount of donor signal recovery upon acceptor photobleaching is related to the quantum yields of the molecules and their overall detection efficiencies.

Figure 2:
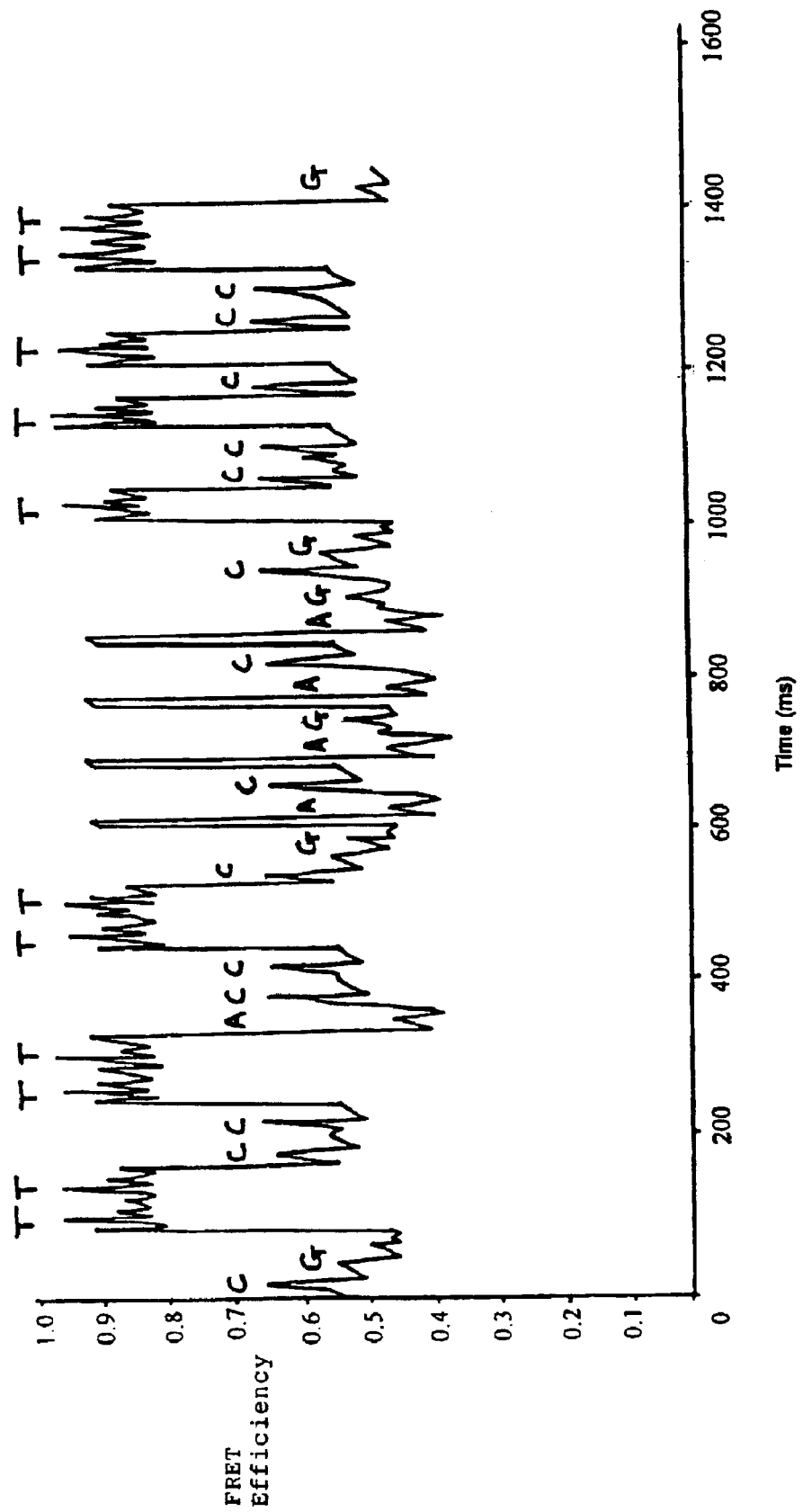
FIG. 2 illustrates a trace taken after fluorescence resonance energy transfer, with each of the peaks representing the detection of a specific nucleotide.

Energy transfer efficiency time trace was then obtained. The FRET efficiency time trace during polymerization of target strand SEQ ID NO: 1 shown in FIG. 2. Reading FIG. 2, the sequence corresponds to the complement of that of SEQ ID NO: 1 (reading right to left, minus that part which hybridises to the primer sequence).

What is claimed is:

1. A method for determining the sequence of a polynucleotide, comprising the steps of:
   i. reacting a target polynucleotide with an enzyme that interacts with and processes along the polynucleotide, under conditions sufficient to induce enzyme activity; and
   ii. detecting conformational changes in the enzyme as the enzyme processes along the polynucleotide, and thereby determining the sequence of the polynucleotide;
   wherein the enzyme comprises a bound fluorescent molecule, the characteristics of which alter as the enzyme undergoes a conformational change, and wherein the target polynucleotide does not comprise a label prior to, during, or after the enzyme processes along the polynucleotide, and wherein if step (i) is carried out in the presence of poly nucleotide monomers, the polynucleotide monomers do not comprise a label.

2. The method according to claim 1, wherein the enzyme is a polymerase enzyme.

3. The method according to claim 1, wherein the enzyme is a helicase enzyme or a primase enzyme.

4. The method according to claim 1, wherein the enzyme is immobilised on a solid support.

5. The method according to claim 4, comprising a plurality of enzymes immobilised on the solid support.

6. The method according to claim 1, wherein the enzyme comprises a bound label that interacts with the bound fluorescent molecule, wherein the degree of infraction is dependent on a conformational change in the enzyme.

7. The method according to claim 6, wherein the bound fluorescent molecule is an energy acceptor and the bound label is an energy donor, or wherein the bound fluorescent molecule is an energy donor and the bound label is an energy acceptor, and wherein step (ii) is carried out by measuring energy transfer between the bound fluorescent molecule and the bound label.

8. The method according to claim 1, wherein step (ii) is carried out using confocal microscopy.

9. The method according to claim 8, wherein step (ii) is carried out by fluorescence imaging.

10. The method according to claim 1, wherein step (ii) is carried out by measuring a polarisation effect consequent on the altered characteristics of the bound fluorescent molecule.

11. The method according to claim 10, wherein step (ii) is carried out by fluorescence polarisation anisotrophy.

12. A solid support comprising at least one immobilised polymerase or helicase enzyme, the enzyme being labelled with at least one fluorescence resonance energy transfer (FRET) donor label and at least one FRET acceptor label.

13. The solid support according to claim 12, wherein the at least one fluorescence resonance energy transfer donor label is a fluorophore.

14. A system for determining a sequence of a polynucleotide, comprising a solid support comprising at least one immobilised polymerase or helicase enzyme, the enzyme being labelled with at least one fluorescence resonance energy transfer (FRET) donor label and at least one FRET acceptor label, and an apparatus for detecting the label.

15. The solid support according to claim 12, wherein the at least one FRET: fluorescence resonance energy transfer acceptor label is a fluorophore.

* * * * *

UNITED STATES PATENT AND TRADEMARK OFFICE
CERTIFICATE OF CORRECTION

PATENT NO. : 6,908,736 B1
DATED : June 21, 2005
INVENTOR(S) : Daniel Henry Densham It is certified that error appears in the above-identified patent and that said Letters Patent is hereby corrected as shown below:

Column 8, line 67 - Column 9, line 1,
"presence of poly nucleotide monomers, the polynucleotide monomers do not" should read -- presence of nucleotide monomers, the nucleotide monomers do not --.

Column 9,
Line 13, "infraction" should read -- interaction --.

Column 10,
Line 21, "one FRET: fluorescence" should read -- one fluorescence --.

Signed and Sealed this

Twenty-third Day of August, 2005

JON W. DUDAS
*Director of the United States Patent and Trademark Office*

SEQUENCE LISTING

<160> NUMBER OF SEQ ID NOS: 2

<210> SEQ ID NO 1
<211> LENGTH: 53
<212> TYPE: DNA
<213> ORGANISM: Artificial Sequence
<220> FEATURE:
<223> OTHER INFORMATION: Template Polynucleotide

<400> SEQUENCE: 1
caaggagagg acgctgtctg tcgaaggtaa ggaacggacg agagaaggga gag        53

<210> SEQ ID NO 2
<211> LENGTH: 17
<212> TYPE: DNA
<213> ORGANISM: Artificial Sequence
<220> FEATURE:
<223> OTHER INFORMATION: Primer Polynucleotide

<400> SEQUENCE: 2
ctctcccttc tctcgtc        17